US005701350A

United States Patent [19]

Popovich

[11] Patent Number: 5,701,350

[45] Date of Patent: Dec. 23, 1997

[54] ACTIVE ACOUSTIC CONTROL IN REMOTE REGIONS

[75] Inventor: Steven R. Popovich, Stoughton, Wis.

[73] Assignee: Digisonix, Inc., Middleton, Wis.

[21] Appl. No.: 657,295

[22] Filed: Jun. 3, 1996

[51] Int. Cl.[6] .......... A61F 11/06

[52] U.S. Cl. .......... 381/71

[58] Field of Search .......... 381/71, 94, 73.1, 381/93; 364/724.19

[56] References Cited

U.S. PATENT DOCUMENTS

| | | | |
|---|---|---|---|
| 4,677,676 | 6/1987 | Eriksson | 381/71 |
| 4,987,598 | 1/1991 | Eriksson | 381/71 |
| 5,278,913 | 1/1994 | Delfosse et al. | 381/71 |
| 5,381,485 | 1/1995 | Elliott | 381/71 |
| 5,390,255 | 2/1995 | Popovich | 381/71 |
| 5,396,561 | 3/1995 | Popovich et al. | 381/71 |
| 5,418,873 | 5/1995 | Eriksson | 381/71 |
| 5,602,929 | 2/1997 | Popovich | 381/71 |

*Primary Examiner*—Curtis Kuntz
*Assistant Examiner*—Vivian Chang
*Attorney, Agent, or Firm*—Andrus, Sceales, Starke & Sawall

[57] ABSTRACT

An active acoustic attenuation system in which the region of desired acoustic control is remote from an error sensor. The invention uses an adjusted error signal from the remote error sensor to update an adaptive control filter. The adaptive control filter drives an output transducer which outputs a secondary input that destructively interferes with and cancels an acoustic disturbance. Adaptation of the adaptive control filter compensates for the error sensor being remote from the region of desired control by adjusting the error signal in accordance with an H filter representing a relationship between a disturbance signal measured by the error sensor and a disturbance signal as would be measured in the region of desired control. The invention includes feedforward and regenerative feedback embodiments, as well as SISO and MIMO embodiments.

20 Claims, 6 Drawing Sheets

ACTIVE ACOUSTIC CONTROL IN REMOTE REGIONS

FIELD OF THE INVENTION

The invention relates to active acoustic attenuation, and in particular to such systems and methods capable of controlling sound or vibration in a region remote from an error sensor.

BACKGROUND OF THE INVENTION

The invention arose during continuing development efforts by the assignee directed toward active acoustic attenuation systems. Active acoustic attenuation involves injecting a cancelling acoustic wave or secondary input, such as sound or vibration, to destructively interfere with and cancel an input acoustic wave or disturbance. The system output is typically sensed with one or more error sensors such as microphones in a sound system or accelerometers in a vibration system. The error sensors generate error signals in response to the sensed system output, and these signals are used to adapt an adaptive control filter. The adaptive control filter inputs one or more reference signals and in mm supplies a correction signal to one or more output transducers such as loudspeakers or shakers. The output transducers inject secondary input to destructively interfere with the disturbance so that the system output at the error sensors is zero or some other desired value. In a feedforward system, the reference signals are obtained using one or more input sensors. In a feedback system, the reference signals are typically error signals from the error sensors or signals derived therefrom.

In some applications, it is not desirable to place the error sensors in the region of desired acoustic control. For instance, a moving piece of machinery having an active acoustic attenuation system may operate in the presence of other objects preventing the mounting of sensors in the far field of the disturbance or region of desired control. In the above example, it is desirable to control or attenuate the acoustic wave in a region remote from the error sensors.

U.S. Pat. No. 5,381,485 entitled "Active Sound Control Systems and Sound Reproduction Systems" to Elliott, describes a system having a monitoring microphone positioned closer to the loudspeaker than to the region of sound reduction. The system disclosed in U.S. Pat. No. 5,381,485 assumes that the wavelength of the sound is large compared to the distance between the monitoring microphone and the desired region of sound reduction, and relies on the assumption that the undesired sound in the region in which the monitoring microphone is located is similar in characteristics to the undesired sound in the region of desired sound reduction. These limitations restrict the applicability of the system.

SUMMARY OF THE INVENTION

The invention is used to actively attenuate an acoustic disturbance in a region of desired control that is remote from the location of an error sensor, without requiring that the disturbance be similar between the location of the error sensor and the region of desired control. In a general sense, the invention accomplishes this by: modeling a relationship between a disturbance source at the location of an error sensor and the disturbance source in the region of desired control with an H filter; using the H filter, in part, to adjust the error signal from the error sensor; and using the adjusted error signal to update the adaptive control filter.

In single input/single output applications, the invention can be summarized as an active acoustic control system having a system input and a system output. The system has an adaptive filter that inputs a reference signal and outputs a correction signal. The correction signal inputs an output transducer, and the output transducer outputs a secondary input that combines with the system input to yield the system output. An error sensor senses the system output at a location remote from the region of desired control and outputs an error signal. The system includes a first C filter ($C_e$) that models a first auxiliary path ($SE_e$) between the output of the adaptive filter and the output of the error sensor. The system also includes a second C filter ($C_r$) that models a second auxiliary path ($SE_r$) between the output of the adaptive filter and the region of desired attenuation. The system also includes an H filter that represents a relationship between a disturbance signal $d_e(k)$ as measured by the error sensor and a disturbance signal $d_r(k)$ as would be measured in the region of desired control. Equivalently, in the case of a single disturbance source, the preferred H filter models a path between the disturbance source and the region of desired control divided by a path between the disturbance source and the output of the error sensor. The correction signal is filtered through the first C filter ($C_e$) to generate a first C-filtered correction signal, and the first C-filtered correction signal is subtracted from the error signal to generate a first intermediate disturbance signal representing the disturbance as sensed by the error sensor. The first intermediate disturbance signal is filtered through the H filter to generate a second intermediate disturbance signal. The correction signal is also filtered through the second C filter ($C_r$) to generate a second C-filtered correction signal, and the second C-filtered correction signal is summed with the second intermediate disturbance signal to generate an adjusted error signal representing the system output in the region of desired control. The adjusted error signal is then used to update the adaptive filter.

In the preferred embodiment, the reference signal is filtered through a copy of the second C filter ($C_r$), and the filtered reference signal is multiplied by the adjusted error signal to provide an error input signal that is used to update the adaptive filter model in a manner consistent with the filtered-X update scheme. If the adaptive filter is an infinite impulse response filter, a similar scheme using the filtered-U update scheme can be used.

In feedforward applications, the system can use an input sensor to provide a reference signal to the adaptive filter. In feedback applications, it is preferred that regenerative feedback be used to derive a reference signal from the adjusted error signal.

The H filter is preferably determined before the system is put into operation, such as testing on the system in the factory, on a prototype, or during an initialization phase occurring before the product using the invention is put into operation. One way of predetermining the H filter is to provide an adaptive H filter and a remote sensor in the region of desired control. A test disturbance should then be provided. The error sensor for the system, which is located in a location remote from the region of desired control, can sense the test disturbance and generate a first signal which inputs the adaptive H filter. The adaptive H filter outputs an H-filtered first signal. The test disturbance is also sensed by the remote sensor located within the region of desired control. The remote sensor generates a second signal. The H-filtered first signal from the adaptive H filter is subtracted from the second signal from the remote sensor to generate a third signal. The third signal is multiplied by the first signal from the error sensor to generate an update signal. The update signal is then used to update the adaptive H filter. This adaptive process is continued until the adaptive H filter satisfactorily models the relationship between the disturbance as measured by the error sensor and region of desired attenuation, or the path between the source of the test disturbance and the region of desired control divided by the path between the source of the test disturbance and the output of the error sensor.

In the event that the H filter is non-causal, it may be desirable to add a delay component to the H filter as well as provide compensating delay filters throughout the remainder of the system.

In multiple input/multiple output applications, a multichannel system can be provided having a plurality of error sensors. Some or all of the error sensors may be located in regions remote from a desired region of control. In this case, the first and second C filters as well as the H filter may be required to be multi-channel adaptive filters.

Other features and advantages of the invention should be apparent to those skilled in the art upon reviewing the following drawings and description thereof.

DETAILED DESCRIPTION OF THE DRAWINGS

Figure 1:
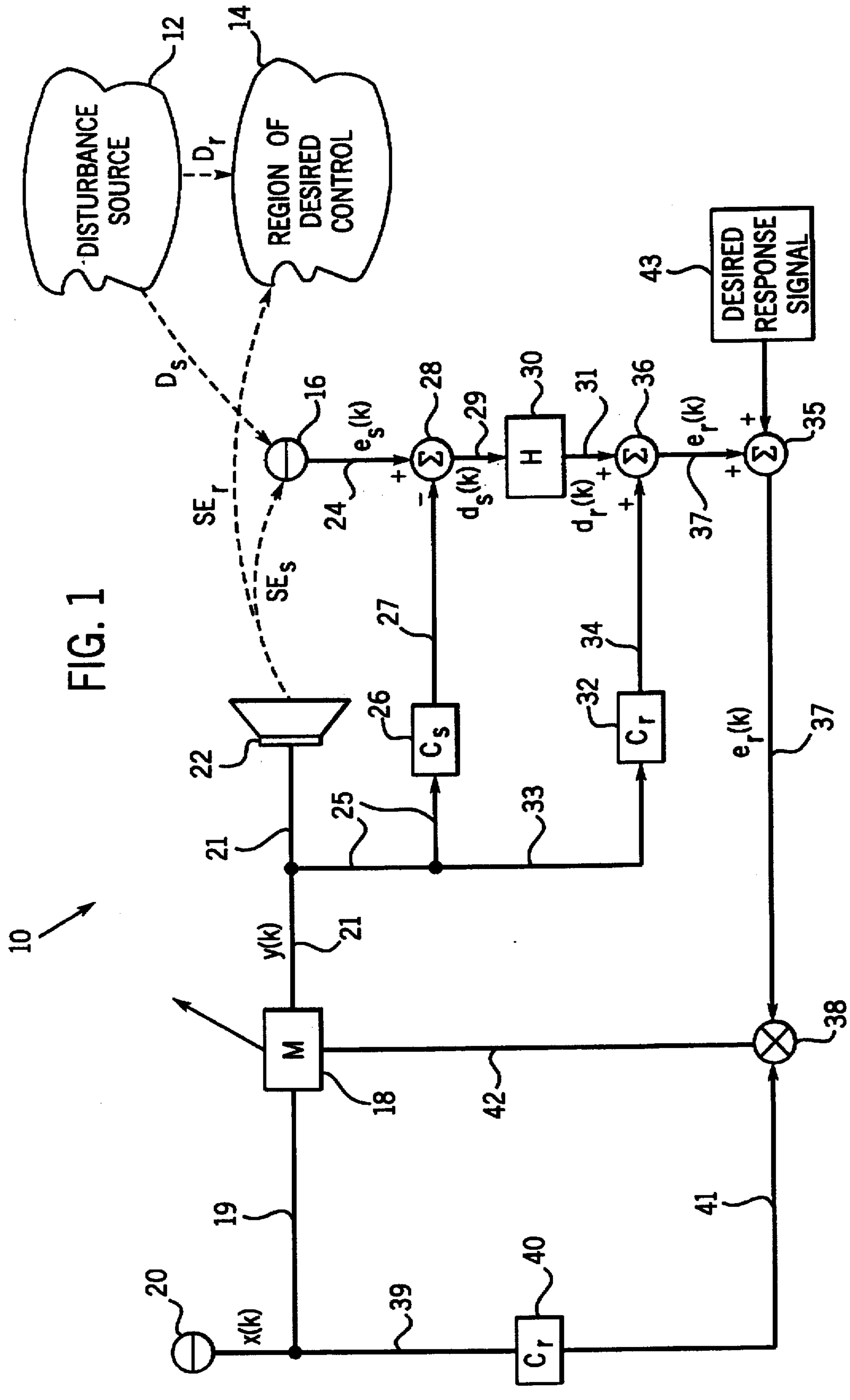
FIG. 1 is a schematic drawing illustrating a single input/single output active acoustic attenuation system in accordance with the invention.

FIG. 1 illustrates a single input/single output active acoustic control system 10 that attenuates an acoustic disturbance $D_r$ propagating from a disturbance source 12 to a region of desired control 14. The system 10 includes an error sensor 16 that is remote from the region of desired control 14. The error sensor 16 senses the disturbance propagating from the disturbance source 12, which is illustrated in FIG. 1 as $D_s$.

The system 10 shown in FIG. 1 includes an adaptive M filter 18 that inputs a reference signal x(k) and outputs a correction signal y(k). The reference signal x(k) inputs the adaptive M model 18 through line 19. The correction signal y(k) inputs the output transducer 22 through line 21. The adaptive M filter 18 shown in FIG. 1 is a finite impulse response filter (FIR), however, other types of adaptive filters such as infinite impulse response (IIR) filters may be used.

The reference signal x(k) is generated by an input sensor 20 that senses an acoustic input to the system 10 and generates the reference signal x(k) in response thereto. In a sound attenuation system, the input sensor 20 and the error sensor 16 are preferably microphones. In a vibration attenuation system, the input sensor 20 and the error sensor 16 are preferably accelerometers.

The correction signal y(k) from the adaptive M filter 18 inputs an output transducer 22. The output transducer 22 outputs a secondary input that combines with the acoustic disturbance to yield an acoustic output for the system. In a sound attenuation system, the output transducer is preferably a loudspeaker. In a vibration attenuation system, the output transducer is typically an electromechanical shaker.

The error sensor 16 senses the system's acoustic output at a location that is remote from the region 14 of desired control, and outputs an error signal $e_s(k)$ in line 24. The error signal $e_s(k)$ in line 24 inputs summer 28.

The correction signal y(k) from the adaptive M filter 18 inputs a first C filter 26 designated by the symbol $C_s$. The fast C filter ($C_s$) 26 models a first auxiliary path $SE_s$ between the output of the adaptive M filter 18 and the output of the error sensor 16. It is preferred that the first C filter ($C_s$) 26 be generated adaptively on-line in accordance with the teachings of U.S. Pat. No. 4,677,676 by Larry J. Eriksson, entitled "Active Attenuation System With On-Line Modeling of Speaker, Error Path and Feedback Path", issued on Jun. 30, 1987, which is incorporated by reference herein, although other methods for determining the first C model ($C_s$) 26 can be used. A first C-filtered correction signal outputs the first C filter ($C_s$) 26 in line 27. The first C-filtered correction signal in line 27 inputs summer 28 where it is subtracted from the error signal $e_s(k)$ in line 24. The summer 28 outputs a first intermediate disturbance signal $d_s(k)$ in line 29 estimating the disturbance from source 12 at the location of the error sensor 16.

The first intermediate disturbance signal $d_s(k)$ inputs an H filter 30. The H filter 30 represents a relationship between the disturbance signal $d_s(k)$ as measured by the error sensor 16 and a disturbance signal $d_r(k)$ as would be measured in the region of desired control 14. Mathematically, the digital H filter 30 is preferably represented by the following equation:

$$H(e^{j\theta}) = \frac{d_r(e^{j\theta})}{d_s(e^{j\theta})}$$

for frequencies where control is desired.

The preferred way of determining the H filter 30 is discussed below in conjunction with FIG. 2. The H filter 30 outputs a second intermediate disturbance signal $d_r(k)$ in line 31.

The correction signal y(k) from the adaptive M filter 18 also inputs a second C filter ($C_r$) 32 through line 33. The second C filter ($C_r$) 32 models a second auxiliary path $SE_r$ between the output of the adaptive M filter 18 and the region of desired control 14. The second C filter ($C_r$) 32 can be predetermined while the system is off-line, either in whole or in part. The second C filter ($C_r$) 32 outputs a second C-filtered correction signal in line 34 representing the action of the secondary input from the output transducer 22 as would be measured in the region of desired control 14.

A second summer 36 inputs the second intermediate disturbance signal $d_r(k)$ from line 31 and the second C-filtered correction signal in line 34, and outputs an adjusted error signal $e_r(k)$ in line 37 representing the system output in the region of desired control 14. The adjusted error signal $e_r(k)$ is the summation of the second intermediate disturbance signal $d_r(k)$ in line 31 and the second C-filtered correction signal in line 34.

The adjusted error signal $e_r(k)$ is typically used directly to generate an update signal for the adaptive M filter 18. Alternatively, it may be desirable to use the technique disclosed in U.S. Pat. No. 5,172,416, entitled "Active Attenuation System With Specified Output Acoustic Wave", by Mark C. Allie, issued on Dec. 15, 1992 and incorporated by reference herein. The technique in U.S. Pat. No. 5,172,416 is used to obtain a desired response to the region of desired control 14. In brief, a desired response signal, block 43, can be combined with the signal in line 37 by summer 35 to effect adaptation of adaptive M filter 18 and obtain the desired response in the region of desired control.

FIG. 1 illustrates a filtered-X update scheme for the adaptive M filter 18. In particular, the adjusted error signal $e_r(k)$ in line 37 inputs multiplier 38. Also, the reference signal x(k) from the input sensor 20 inputs a copy 40 of the second C filter ($C_r$) through line 39. The copy 40 of the second C filter ($C_r$) outputs a filtered reference signal in line 41 that inputs multiplier 38 along with the adjusted error signal $e_r(k)$. The multiplier 38 outputs an update signal in line 42 that is used to update the adaptive M filter 18.

Figure 2:
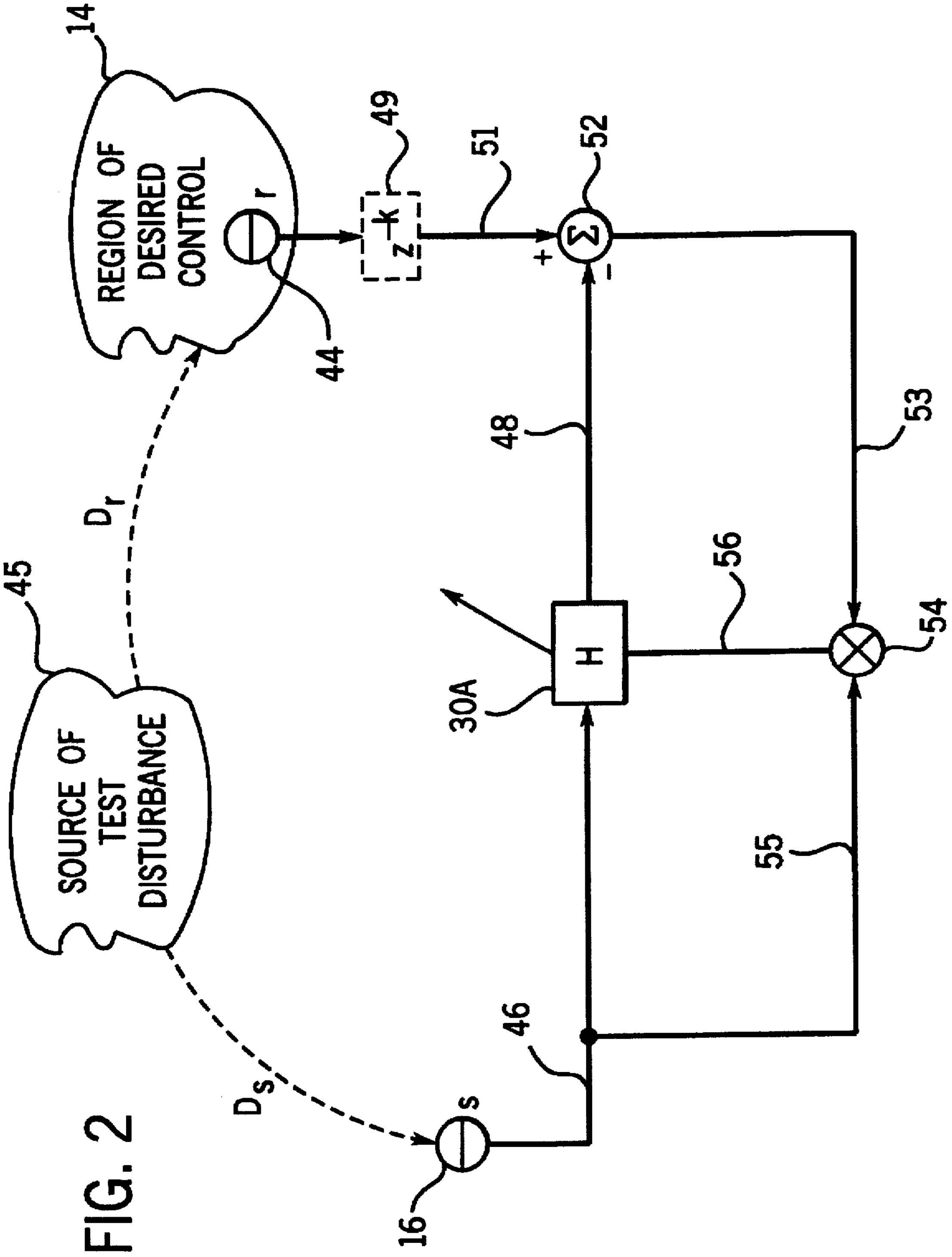
FIG. 2 is a schematic drawing illustrating a way of adaptively determining the H filter shown in FIG. 1 before the system is in operation.

FIG. 2 illustrates the preferred way of adaptively determining the H filter 30. As previously noted, the H filter is preferably determined before the system 10 is put into operation by adaptively testing the system 10, or a prototype of the system, before the system 10 is put into use. To do this, a remote error sensor 44 is placed in the region of desired control 14. A test disturbance is then provided from source 45, which can be the actual disturbance source 12 or an artificially generated disturbance source. The test disturbance is sensed both by the remote error sensor 44 in the region of desired control 14 and the error sensor 16 that is used when the system 10 is in operation. The error sensor 16 generates a signal in line 46 that inputs an adaptive H filter 30*a*. The adaptive H filter 30*a* outputs an H-filtered first signal in line 48. The remote error sensor 44 in the region of desired control 14 senses the disturbance, and outputs a second signal in line 51. The H-filtered first signal in line 48 is subtracted from the second signal in line 51 in summer 52. A third signal outputs summer 52 in line 53 and inputs a multiplier 54. The first signal in line 46 also inputs the multiplier 54 through line 55. The multiplier 54 outputs an update signal in line 56 that is used to update the adaptive H filter 30*a*. The adaptive process is continued in this manner until the H filter satisfactorily models the relationship between the disturbance signal $d_r(k)$ as measured by the error sensor 16 and the disturbance signal $d_r(k)$ as measured by the remote sensor 44 in the region of desired control 14. Once the H filter 30*a* is determined in accordance with the scheme shown in FIG. 2, the H filter 30*a* is used when the system is in operation as H filter 30 in FIG. 1.

Figure 3:
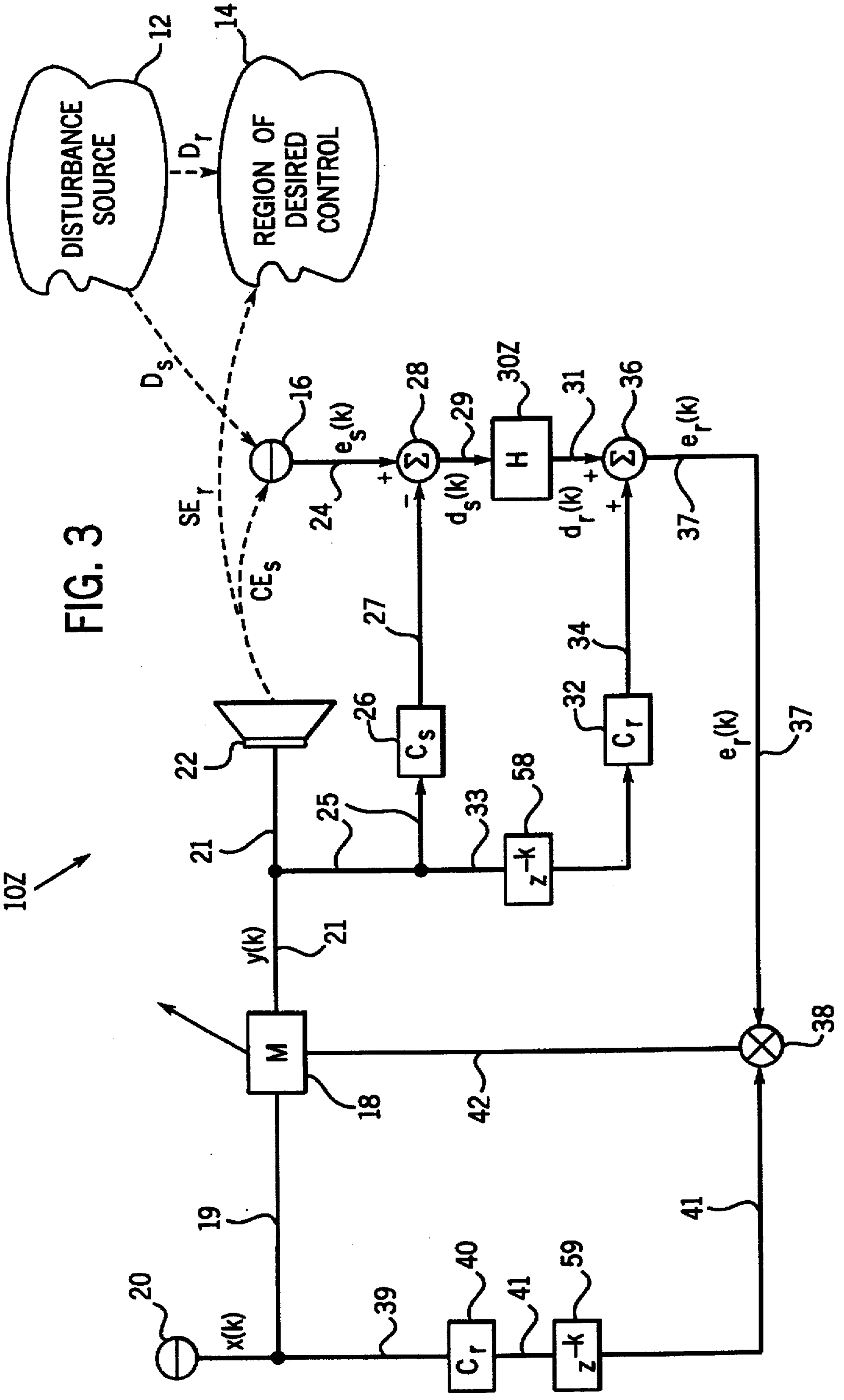
FIG. 3 is a schematic drawing illustrating an embodiment of the invention in which the H filter includes a delay component.

FIG. 3 illustrates a system 10Z that is similar in many respects to the system 10 shown in FIG. 1, and like reference numerals are used where appropriate to facilitate understanding. The system 10Z shown in FIG. 3 should be used in the event that the H filter 30 in FIG. 1 is non-causal. In that case, delay components should be added to the system as shown in the system 10Z in FIG. 3. An example of when the system would probably be non-causal, is when the region of desired control 14 is closer to a broadband disturbance source 12 than the error sensor 16.

In particular, system 10Z in FIG. 3 uses an H filter 30Z with a delay component $z^{-k}$. In addition, compensating delay filters 58 and 59 are added to the system. In particular, compensating delay filter 58 is inserted in line 33. Thus, in system 10Z, the correction signal y(k) from the adaptive M filter 18 is filtered through delay filter 58 before inputting the second C filter ($C_r$) 32. Also, the filtered reference signal in line 41 from the copy 40 of the second C filter ($C_r$) is filtered through delay filter 59 before inputting the multiplier 38.

The H filter 30Z in FIG. 3 is given by H, and can be determined in accordance with FIG. 2 by placing a delay block $z^{-k}$ (shown in phantom by reference numeral 49) in line 51, FIG. 2, to delay the second signal in line 51 which is transmitted from the remote error sensor 44 in the region of desired control 14.

Figure 4:
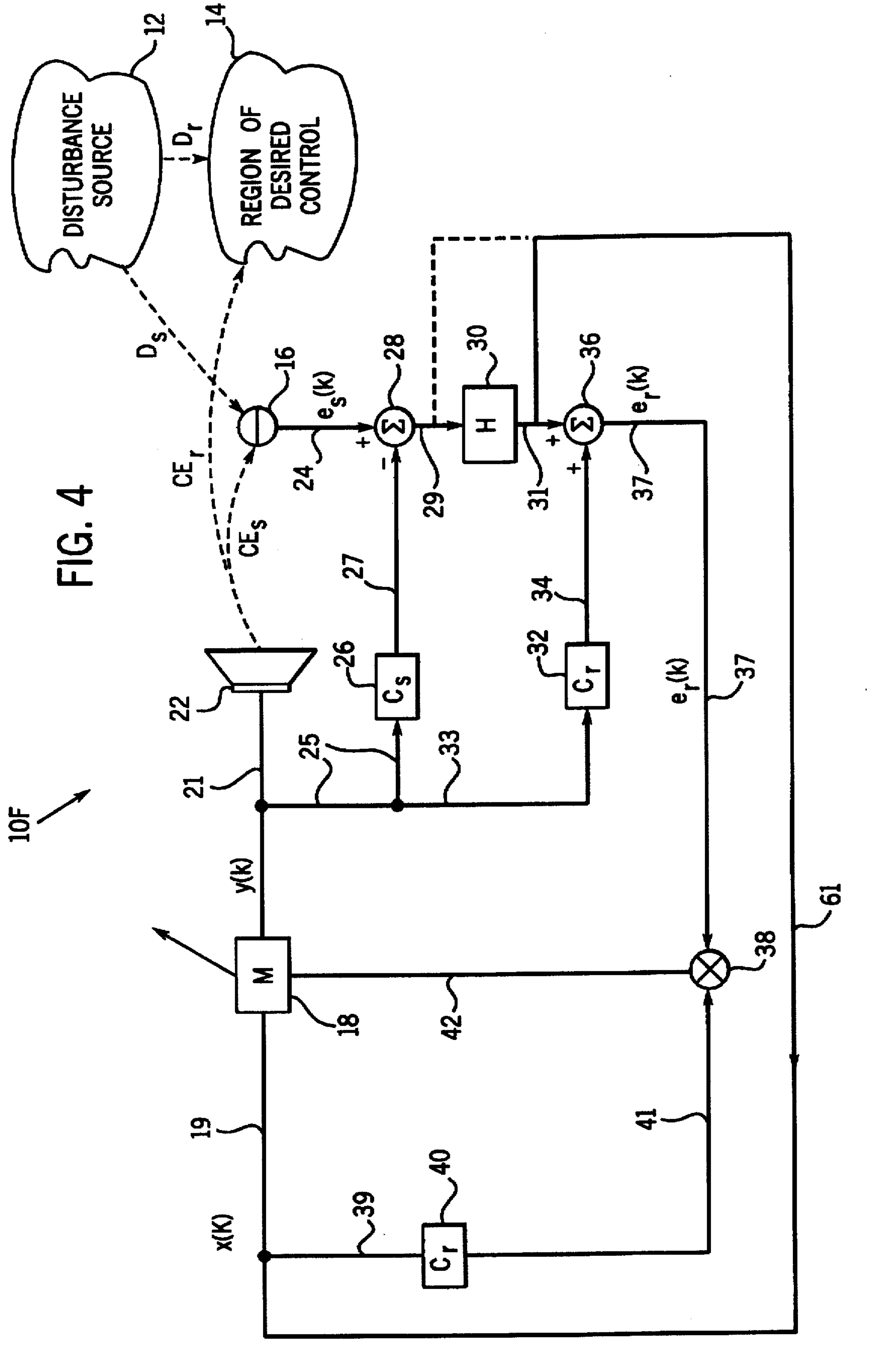
FIG. 4 is a schematic drawing illustrating an embodiment of the invention in which the reference signal is derived using a regenerative feedback method.

FIG. 4 illustrates an active acoustic attenuation system 10F in which the reference signal x(k) is derived using a regenerative feedback method. In many respects, the system 10F shown in FIG. 4 is similar to the system 10 shown in FIG. 1 and like reference numerals are used where appropriate to facilitate understanding.

Although other types of feedback methods may be used in conjunction with the invention, the preferred method is illustrated in FIG. 4. In FIG. 4, the second intermediate disturbance signal $d_r(k)$ in line 31 is transmitted through line 61 and through line 19 to the adaptive M filter 18, and is also transmitted through line 39 to the copy 40 of the second C filter ($C_r$). A filtered reference signal outputs the copy 40 of the second C filter ($C_r$) in line 41, and inputs multiplier 38. Alternatively, the first intermediate disturbance signal $d_r(k)$ in line 29 can be transmitted through line 61 in lieu of the second intermediate disturbance signal $d_r(k)$. Other regenerative feedback methods such as those disclosed in U.S. Pat. No. 5,390,255 by Steven R. Popovich entitled "Active Acoustic Attenuation System With Error And Model Copy Input" and issued on Feb. 14, 1995, herein incorporated by reference, can also be used in accordance with the invention.

Figure 5:
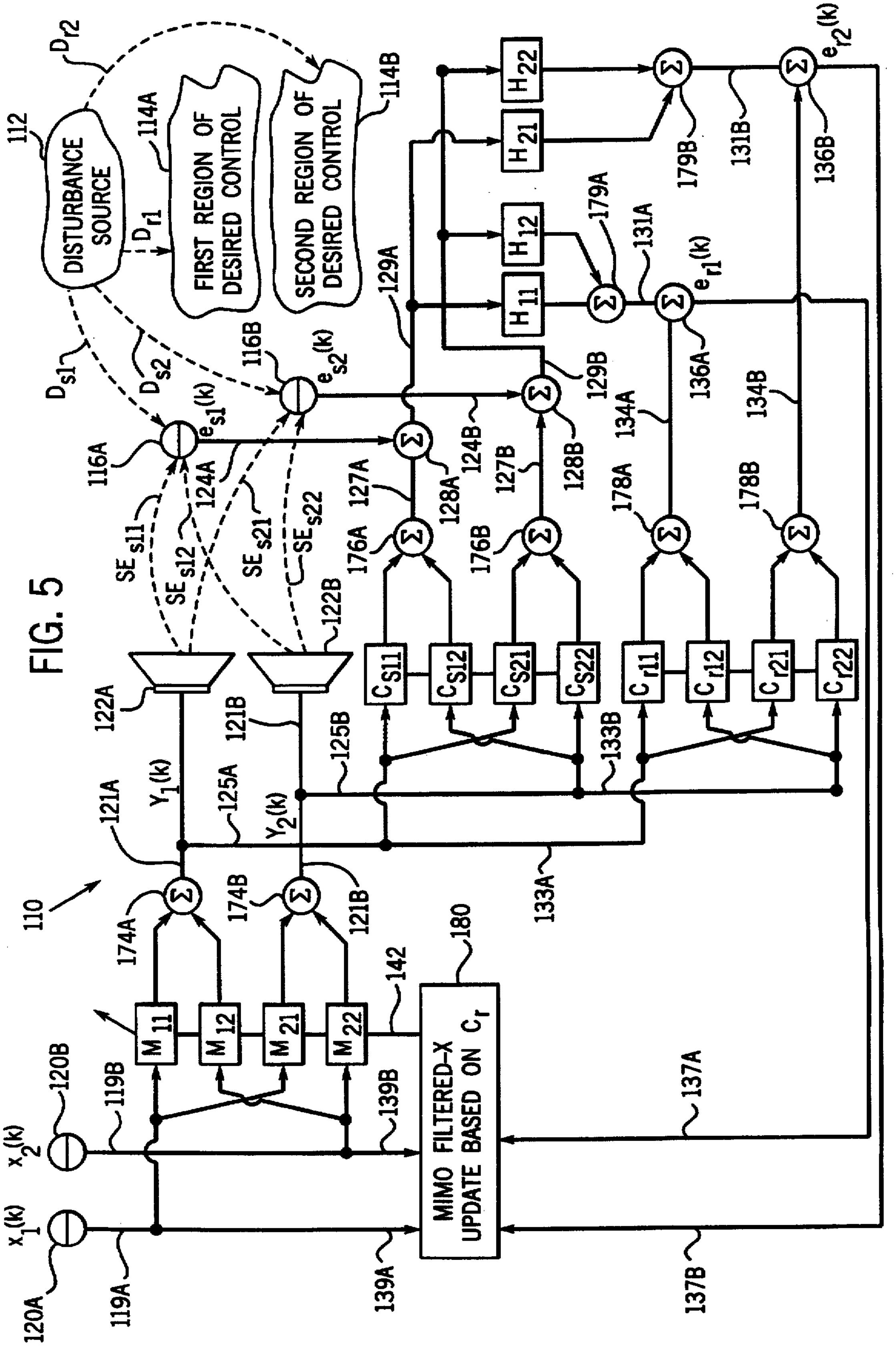
FIGS. 5 and 6 are schematic drawings illustrating a multiple input/multiple output active acoustic attenuation system in accordance with the invention.

FIG. 5 illustrates the invention cancelling an acoustic disturbance having evanescent modal components and non-evanescent modal components propagating along a waveguide 66. The system 10M shown in FIG. 5 is again similar in many respects to the system 10 shown in FIG. 1 and like reference numerals are used where appropriate to facilitate proper understanding.

Figure 6:
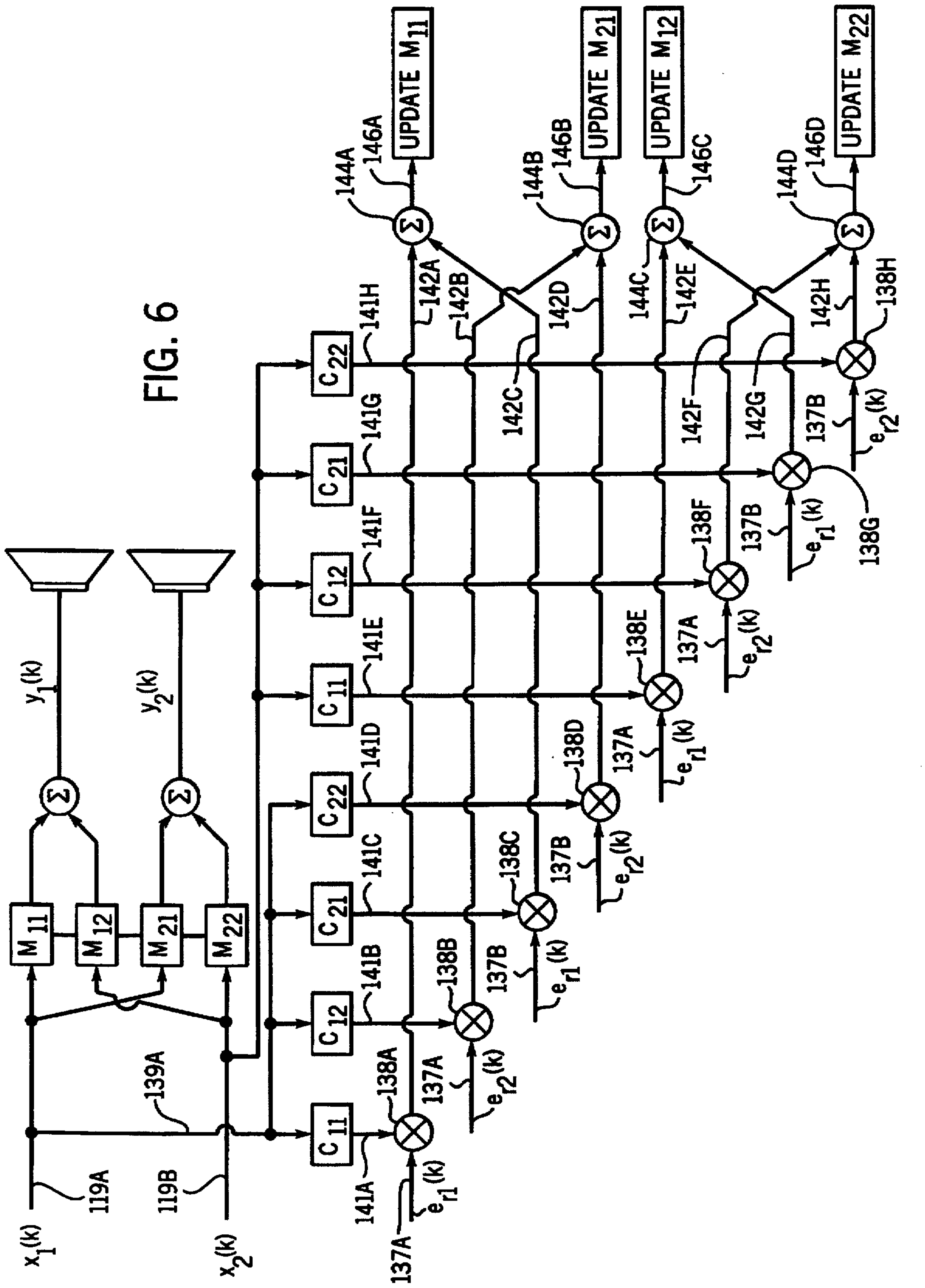

FIGS. 5 and 6 illustrate a multiple input/multiple output active acoustic attenuation system 110 similar to the SISO system shown in FIG. 1. The MIMO system 110 shown in FIGS. 6 and 7 is a 2×2×2×2 system, including: two input sensors 120*a* and 120*b*, two output transducers 122*a* and 122*b*, two error sensors 116*a* and 116*b*, and two separate regions of desired control 114*a* and 114*b*. The 2×2×2×2 system 110 shown in FIG. 5 is merely an example of a MIMO system, and it should be understood that the number of input sensors, output transducers, error sensors, and regions of desired control can be varied depending on the requirements for the specific application. For instance, it may be desirable to have a large number of error sensors 116*a*, 116*b* . . . and a relatively few number of regions of desired control 114*a*, 114*b* . . . or vice versa.

The system shown in FIG. 5 includes a plurality of input sensors 120*a* and 120*b*. Input sensor 120*a* generates a reference signal $x_1(k)$ in line 119*a*, and input sensor 120*b* generates a reference signal $x_2(k)$ in line 119*b*. The system 110 includes a multi-channel adaptive M filter having a plurality of channels $M_{11}$, $M_{12}$, $M_{21}$, and $M_{22}$. The reference signal $x_1(k)$ from the first input sensor 120*a* is transmitted through line 119*a* to adaptive M filter channels $M_{11}$ and $M_{21}$. The reference signal $x_2(k)$ from the second input sensor 120*b* is transmitted through line 119*b* to adaptive M filter channels $M_{12}$ and $M_{22}$. Adaptive M filter channels $M_{11}$ and $M_{12}$ output a signal that inputs summer 174*a*. Summer 174*a* outputs a first correction signal $y_1(k)$ in line 121*a*. Adaptive M model channels $M_{21}$ and $M_{22}$ output a signal that inputs summer 174*b*. Summer 174*b* outputs a second correction signal $y_2(k)$ in line 121*b*.

The first correction signal $y_1(k)$ in line 121*a* inputs a first output transducer 122*a*. The second correction signal $y_2(k)$ in line 121*b* inputs a second output transducer 122*b*. Each of the output transducers 122*a* and 122*b* outputs a secondary input which combines with the acoustic disturbance from the disturbance source 112 to yield an acoustic output for the system. The acoustic output for the system 110 is sensed by a first error sensor 116a located a region remote from a region of desired control such as regions 114a and 114b, and a second error sensor 116b also located in a region remote from a region of desired control. Although the system shown in FIG. 6 does not show any error sensor located within a region of desired control as in a conventional system, it is certainly within the scope of the invention to locate one or more error sensors within a region of desired control while having one or more error sensor 116a and 116b located remote from a region of desired control.

The first error sensor 116a generates a first error signal $e_{s1}(k)$ in line 124a. The second error sensor 116b generates a second error signal $e_{s2}(k)$ in line 124b.

As shown in FIG. 5, the first error sensor 116a senses the acoustic combination of the disturbance $D_{s1}$ from the source of the disturbance 112 and the secondary inputs from the first output transducer 122a and the second output transducer 122b (i.e. $SE_{s11}$ and $SE_{s12}$). The second error sensor 116 senses the acoustic combination of the disturbance $D_{s2}$ from the source of the disturbance 112 and the secondary inputs from the first output transducer 122a and the second output transducer 122b (i.e. $SE_{s21}$ and $SE_{s22}$).

The first correction signal $y_1(k)$ from line 121a is also transmitted through line 125a to channels $C_{s11}$ and $C_{21}$ of a first multi-channel C filter. The second correction signal $y_2(k)$ from line 121b is transmitted through line 125b to channels $C_{s12}$ and $C_{s22}$ of the first multi-channel C filter. The first C filter channels $C_{s11}$, $C_{s12}$, $C_{s21}$ and $C_{s22}$ model auxiliary paths including the corresponding secondary input paths $SE_{s11}$, $SE_{s12}$, $SE_{s21}$ and $SE_{s22}$ between the output transducers 122a and 122b and the error sensors 116a and 116b. First C model channels $C_{s11}$ and $C_{s12}$ each output a signal that is transmitted to summer 176a. Summer 176a outputs one of two first C-filtered correction signals in line 127a. First C model channels $C_{s21}$ and $C_{s22}$ each output a signal that inputs summer 176b. Summer 176b outputs another first C-filtered correction signal in line 127b. The first C-filtered correction signals in 127a and 127b constitute a set of two first C-filtered correction signals. The first C-filtered correction signal in line 127a is subtracted from the first error signal in 124a in summer 128a. One of two first intermediate disturbance signals outputs summer 128a in line 129a. Likewise, the first C-filtered signal in line 127b is subtracted from the second error signal $e_{s2}(k)$ in line 124b in summer 128b, and another first intermediate disturbance signal outputs summer 128b in line 129b. The signals in line 129a and 129b constitute a set of two first intermediate disturbance signals.

The system 110 includes a multi-channel H filter having channels $H_{11}$, $H_{12}$, $H_{21}$ and $H_{22}$. The signal in line 129a inputs H filter channels $H_{11}$ and $H_{21}$. The signal in line 129b inputs H-filtered channels $H_{12}$ and $H_{22}$. H filter channels $H_{11}$ and $H_{12}$ output a signal to summer 179a which outputs one of two second intermediate disturbance signals in line 131a. H filter channels $H_{21}$ and $H_{22}$ each output a signal to summer 179b which outputs another second intermediate disturbance signal in line 131b. The signals in lines 131a and 131b constitute a set of two intermediate disturbance signals.

The system 110 also includes a second multi-channel C filter having a plurality of channels $C_{r11}$, $C_{r12}$, $C_{r21}$ and $C_{r22}$. The first correction signal $y_1(k)$ in line 121a is transmitted through lines 125a and 133a to second C filter channels $C_{r11}$ and $C_{r21}$. The second correction signal $y_2(k)$ in line 121b is transmitted through lines 125b and 133b to second C filter channels $C_{r12}$ and $C_{r22}$. Second C filter channels $C_{r11}$ and $C_{r12}$ each output a signal that is transmitted to summer 178a. Summer 178a outputs one of two second C-filtered correction signals in line 134a. Second C filter channels $C_{r21}$ and $C_{r22}$ each output a signal that is transmitted to summer 178b. Summer 178b outputs another second C-filtered signal in line 134b. The signals in line 134a and 134b constitute a set of two second C-filtered correction signals. The second C-filtered correction signal in line 134a is summed with the second intermediate disturbance signal in line 131a in summer 136a to generate one of two adjusted error signals $e_{r1}(k)$ in line 137a. The other of the second C filter correction signals in line 134b sum together with the second intermediate disturbance signal in line 131b in summer 136b to generate a second adjusted error signal $e_{r2}(k)$ in line 137b.

FIG. 5 indicates that the adjusted error signals $e_{r1}(k)$ in line 137a and $e_{r2}(k)$ in line 137b are used to update the adaptive M filter channels $M_{11}$, $M_{12}$, $M_{21}$, and $M_{22}$ based on a MIMO filtered-X update scheme, block 180. The MIMO filtered-X update for the system 110 is shown in greater detail in FIG. 6. In particular, the first reference signal $x_1(k)$ is transmitted from line 119a through 139a to copies of the second C filter channels $C_{r11}$, $C_{r12}$, $C_{r21}$ and $C_{r22}$. The copy of channel $C_{r11}$ inputting $x_1(k)$ outputs a filtered reference signal in line 141a which is transmitted to multiplier 138a as a regressor signal for the first adjusted error signal $e_{r1}$ from line 137a. The multiplier 138a outputs a signal in line 142a that inputs summer 144a. The copy of channel $C_{r12}$ inputting $x_1(k)$ outputs a filtered reference signal in line 141b which is transmitted to a multiplier 138b as a regressor signal for the first adjusted error signal $e_{r1}$ from line 137a. The multiplier 138b outputs a signal in line 142b that inputs summer 144b. The copy of channel $C_{r22}$ inputting $x_1(k)$ outputs a filtered reference signal in line 141c which is transmitted to a multiplier 138c as a regressor signal for the second adjusted error signal $e_{r2}$ from line 137b. The multiplier 138c outputs a signal in line 142c that inputs summer 144a. Summer 144a outputs an error input signal in line 146a that is used to update the adaptive M filter channel $M_{11}$. The copy of channel $C_{r22}$ inputting $x_1(k)$ outputs a filtered reference signal in line 141d which is transmitted to multiplier 138d as a regressor signal for the second adjusted error signal $e_{r2}$ from line 138b. The multiplier 138d outputs a signal in line 142d that inputs summer 144b. The summer 144b outputs an error input signal in line 146b that is used to update the adaptive M filter channel $M_{21}$.

The second reference signal $x_2(k)$ in line 119b is transmitted through 139b to copies of second C filter channels $C_{r11}$, $C_{r12}$, $C_{r21}$ and $C_{r22}$. The copy of channel $C_{r11}$ inputting $x_2(k)$ outputs a filtered reference signal in line 141e which is transmitted to multiplier 138e as a regressor signal for the first adjusted error signal $e_{r1}$ from line 137a. The multiplier 138e outputs a signal in line 142e that inputs summer 144c. The copy of channel $C_{r12}$ inputting $x_2(k)$ outputs a filtered reference signal in line 141f which is transmitted to multiplier 138f as a regressor signal for the first adjusted error signal $e_{r1}$ from line 137a. The multiplier 138f outputs a signal in line 142f that inputs summer 144d. The copy of channel $C_{r21}$ inputting $x_1(k)$ outputs a filtered reference signal in line 141g which is transmitted to multiplier 138g as a regressor signal for the second adjusted error signal $e_{r2}$ from line 137b. The multiplier 138g outputs a signal in line 142g that inputs summer 144c. Summer 144c outputs an error input signal in line 146c that is used to update the adaptive M filter channel $M_{12}$. The copy of channel $C_{r22}$ inputting $x_2(k)$ outputs a filtered reference signal in line 141h which is transmitted to multiplier 138h as a regressor signal for the second adjusted error signal $e_{r2}$ from line 137*b*. The multiplier 138*h* outputs a signal in line 142*h* that inputs summer 144*d*. The summer 144*d* outputs an error input signal in line 146*d* that is used to update the adaptive M filter channel $M_{22}$.

It should be readily apparent to those skilled in the art that the determination of the first multi-channel C model ($C_e$) can be determined adaptively on-line. It should also be understood that the multi-channel H filter can be determined by applying MIMO techniques to the method disclosed in FIG. 2 for the SISO system. The same should be apparent to those skilled in the art for determining the second multi-channel C model ($C_r$).

It is recognized that various equivalents, alternatives and modifications of the invention are possible and should be considered to fall within the scope of the claims.

I claim:

1. An active acoustic attenuation system for attenuating an acoustic disturbance from a disturbance source in a region of desired control that is remote from an error sensor, the system comprising:

an adaptive filter that inputs a reference signal and outputs a correction signal;

an output transducer that inputs the correction signal and outputs a secondary input that combines with an acoustic disturbance to yield acoustic output;

an error sensor that senses the acoustic output at a first location remote from a region of desired control, and outputs an error signal in response thereto;

a first C filter modeling a first auxiliary path between the output of the adaptive filter and the output of the error sensor, the first C filter inputting the correction signal and outputting a first C-filtered correction signal;

a second C filter modeling a second auxiliary path between the output of the adaptive filter and the region of desired control, the second C filter inputting the correction signal and outputting a second C-filtered correction signal;

a first summer that inputs the error signal and the first C-filtered correction signal and outputs a first intermediate disturbance signal;

an H filter representing a relationship between a disturbance signal as measured by the error sensor and a disturbance signal as would be measured in the region of desired control, the H filter inputting the first intermediate disturbance signal and outputting a second intermediate disturbance signal; and a second summer that inputs the second intermediate disturbance signal and the second C-filtered correction signal and outputs an adjusted error signal that is used to update the adaptive filter.

2. An active acoustic attenuation system as recited in claim 1 wherein the H filter is predetermined before the system is in operation.

3. An active acoustic attenuation system as recited in claim 1 wherein the first summer subtracts the first C-filtered correction signal from the error signal to generate the first intermediate disturbance signal.

4. An active acoustic attenuation system as recited in claim 1 further comprising:

a copy of the second C filter which models the second auxiliary path between the output of the adaptive filter and the region of desired control, the copy of the second C filter inputting the reference signal and outputting a filtered reference signal; and a multiplier that inputs the filtered reference signal and the adjusted error signal and outputs an error input signal that is used to update the adaptive filter.

5. An active acoustic attenuation system as recited in claim 1 further comprising a third summer that combines a desired response signal with the adjusted error signal.

6. An active acoustic attenuation system as recited in claim 1 wherein the second intermediate disturbance signal inputs the adaptive filter as the reference signal.

7. An active acoustic attenuation system as recited in claim 1 wherein the first intermediate disturbance signal inputs the adaptive filter as the reference signal.

8. An active acoustic attenuation system as recited in claim 1 wherein the reference signal is derived from the adjusted error signal using regenerative feedback.

9. An active acoustic attenuation system as recited in claim 4 wherein:

the H filter is modeled based on a delayed version of the disturbance in the region of desired control;

the correction signal is filtered through a first delay filter before inputting the second C filter; and the filtered reference signal is filtered through a second delay filter before inputting the multiplier.

10. An active acoustic attenuation system as recited in claim 1 wherein the adaptive filter is an FIR filter.

11. An active acoustic attenuation system as recited in claim 1 wherein the adaptive filter is an IIR filter.

12. An active acoustic attenuation system as recited in claim 1 wherein the first C filter is determined adaptively on line when the system is in operation.

13. An active acoustic attenuation system as recited in claim 1 further comprising an input sensor that senses the system input and generates the reference signal in response thereto.

14. An active acoustic attenuation system for attenuating an acoustic disturbance from a disturbance source in a region of desired control that is remote from an error sensor, the system comprising:

an adaptive filter that inputs a reference signal and outputs a correction signal;

an output transducer that inputs the correction signal and outputs a secondary input that combines with an acoustic disturbance to yield acoustic output;

an error sensor that senses the acoustic output at a first location remote from a region of desired control, and outputs an error signal in response thereto;

a first C filter modeling a first auxiliary path between the output of the adaptive filter and the output of the error sensor, the first C filter inputting the correction signal and outputting a first C-filtered correction signal;

a second C filter modeling a second auxiliary path between the output of the adaptive filter and the region of desired control, the second C filter inputting the correction signal and outputting a second C-filtered correction signal;

a first summer that inputs the error signal and the first C-filtered correction signal and outputs a first intermediate disturbance signal;

an H filter representing a relationship between a path from the disturbance source to the error sensor and a path from the disturbance source to the region of desired control, the H filter inputting the first intermediate disturbance signal and outputting a second intermediate disturbance signal; and a second summer that inputs the second intermediate disturbance signal and the second C-filtered correction signal and outputs an adjusted error signal that is used to update the adaptive filter.

15. A multi-channel active acoustic attenuation system for attenuating an acoustic disturbance from a disturbance source in one or more regions of desired control that are remote from any error sensors in the system, the system comprising:

an adaptive filter having a plurality of channels, the adaptive filter inputting one or more reference signals and outputting one or more correction signals;

one or more output transducers, each output transducer inputting one of the correction signals and outputting a secondary input which combine with the acoustic disturbance to yield acoustic output;

one or more error sensors, each sensing the acoustic output at a location remote from one or more regions of desired control and each outputting an error signal in response thereto;

a first C filter having a plurality of channels, each channel of the first C filter modeling an auxiliary path between one of the output transducers and one of the error sensors, the first C filter inputting the correction signals and outputting a set of one or more first C-filtered correction signals;

a second C filter having a plurality of channels, each channel of the second C filter modeling an auxiliary path between one of the output transducers and one of the regions of desired control, the second C filter inputting the correction signals and outputting a set of one or more second C-filtered correction signals;

a first set of one or more summers that inputs the one or more error signals and the set of one or more first C-filtered correction signals and outputs a set of one or more first intermediate disturbance signals;

an H filter having a plurality of channels, each channel of the H filter representing a relationship from the disturbance source to one of the error sensors and a path from the disturbance source to one of the regions of desired control, the H filter inputting the set of one or more first intermediate disturbance signals and outputting a set of one or more second intermediate disturbance signals; and a second set of one or more summers that inputs the set of one or more second intermediate disturbance signals and the set of one or more second C-filtered correction signals and outputs a set of one or more adjusted error signals that is used to update the plurality of channels in the adaptive filter.

16. A multi-channel active acoustic attenuation system as recited in 15 wherein the H filter represents a relationship between the disturbance as measured by the one or more error sensors and the disturbance as would be measured within the one or more regions of desired control.

17. A multi-channel active acoustic attenuation system as recited in claim 15 further comprising at least one error sensor located within a region of desired control.

18. In an active acoustic attenuation system, a method of attenuating an acoustic disturbance in a region of desired control that is remote from an error sensor, the method comprising the steps of:

inputting a reference signal to an adaptive filter;

outputting a correction signal from the adaptive filter;

inputting the correction signal to an output transducer;

outputting a secondary input from the output transducer to combine with the acoustic disturbance and yield an acoustic output;

sensing the acoustic output with an error sensor at a location remote from a region of desired control and generating an error signal in response thereto;

filtering the correction signal through a first C filter modeling an auxiliary path between the output of the adaptive filter and the output of the error sensor to generate a first C-filtered correction signal;

subtracting the first C-filtered correction signal from the error signal to generate a first intermediate disturbance signal;

filtering the correction signal through a second C filter modeling a second auxiliary path between the output of the adaptive filter and the region of desired control to generate a second C-filtered correction signal;

filtering the first intermediate error signal through an H filter to generate a second intermediate disturbance signal, the H filter representing a relationship between a path from the source of the acoustic disturbance to the error sensor and a path from the source of the acoustic disturbance to the region of desired control;

subtracting the second C-filtered correction signal from the second intermediate disturbance signal to generate an adjusted error signal; and using the adjusted error signal to update the adaptive filter.

19. The method as recited in claim 18 wherein the H filter represents a relationship between a disturbance signal as measured by the error sensor and a disturbance signal as would be measured in the region of desired control.

20. The method as recited in claim 18 further comprising the step of determining the H filter before the active acoustic attenuation system is in operation by:

placing a remote sensor within the region of desired control;

providing a disturbance that can be sensed by the error sensor located in the location remote from the region of desired control and by the remote sensor located within the region of desired control;

sensing the disturbance with the error sensor located in the location remote from the region of desired control and generating a first signal in response thereto;

inputting the first signal to an adaptive H filter;

outputting an H-filtered first signal from the adaptive H filter;

sensing the disturbance with the remote sensor located within the region of desired control and generating a second signal in response thereto;

subtracting the H-filtered first signal from the second signal to generate a third signal;

multiplying the third signal by the first signal to generate an update signal; and using the update signal to update the adaptive H filter.

* * * * *